United States Patent
Jiang et al.

(10) Patent No.: US 7,767,461 B2
(45) Date of Patent: Aug. 3, 2010

(54) APPARATUS AND METHOD FOR MEASURING CONCENTRATIONS OF SCALE-FORMING IONS

(75) Inventors: Li Jiang, Ridgefield, CT (US); Timothy Gareth John Jones, Cambridge (GB); Andrew Meredith, Cambridge (GB); Markus Pagels, Cambridge (GB); Amilra Prasanna De Silva, Belfast (GB)

(73) Assignee: Schlumberger Technology Corporation, Ridgefield, CT (US)

( * ) Notice: Subject to any disclaimer, the term of this patent is extended or adjusted under 35 U.S.C. 154(b) by 1051 days.

(21) Appl. No.: 10/564,939

(22) PCT Filed: Jul. 12, 2004

(86) PCT No.: PCT/GB2004/003040

§ 371 (c)(1),
(2), (4) Date: Jul. 17, 2006

(87) PCT Pub. No.: WO2005/014977

PCT Pub. Date: Feb. 17, 2005

(65) Prior Publication Data

US 2007/0065337 A1    Mar. 22, 2007

(30) Foreign Application Priority Data

Jul. 24, 2003   (GB) .................. 0317260.8

(51) Int. Cl.
*G01N 33/20*   (2006.01)
(52) U.S. Cl. ............. 436/79; 436/150; 422/82.01
(58) Field of Classification Search ............ 422/82.01; 436/79, 150
See application file for complete search history.

(56) References Cited

U.S. PATENT DOCUMENTS

| 5,120,421 A | 6/1992 | Glass et al. |
| 5,296,123 A | 3/1994 | Reddy et al. |
| 5,437,772 A | 8/1995 | De Castro et al. |
| 5,676,820 A | 10/1997 | Wang et al. |

(Continued)

FOREIGN PATENT DOCUMENTS

| DE | 198 29 415 A1 | 1/2000 |
| DE | 198 54 651 C1 | 5/2000 |
| GB | 2 362 469 A | 11/2001 |
| GB | 2 373 248 A | 9/2002 |

(Continued)

OTHER PUBLICATIONS

Eisenman et al Ion binding and ion transport produced by neutral lipid-soluble molecules Progress in surface and membrane science, edited by Danielli et al, vol. 6, Academic Press, New York, 1973, pp. 139-241.

(Continued)

*Primary Examiner*—Lyle A Alexander
(74) *Attorney, Agent, or Firm*—James McAleenan; Vincent Loccisano; Brigid Laffey (57) ABSTRACT

This invention relates to methods and apparatus for determination of ion concentrations, particularly in downhole water from hydrocarbon wells, aquifers etc. It is useful in a wide range of applications, including predicting the formation of scale and fingerprinting waters from different sources. More particularly, the invention relates to the use of ligands whose electronic configuration is altered by the binding of the scaling ions within a water sample. These alterations are detected, for example by electrochemical means, and are indicative of the concentration of scaling ions in the sample.

24 Claims, 6 Drawing Sheets

U.S. PATENT DOCUMENTS

| | | | |
|---|---|---|---|
| 5,736,650 | A | 4/1998 | Hiron et al. |
| 5,829,520 | A | 11/1998 | Johnson |
| 6,004,442 | A | 12/1999 | Choulga et al. |
| 6,200,444 | B1 | 3/2001 | Ahlers et al. |
| 2001/0042693 | A1 | 11/2001 | Onitskansky et al. |

FOREIGN PATENT DOCUMENTS

| | | |
|---|---|---|
| GB | 2 391 314 A | 2/2004 |
| JP | 60-5279 A | 1/1985 |
| WO | 01/98630 A1 | 12/2001 |
| WO | 02/090958 A2 | 11/2002 |
| WO | 02/090958 A3 | 2/2003 |

OTHER PUBLICATIONS

Helgeson et al Complete optical resolution by differential complexation in solution between a chiral cyclic polyether and an alpha-amino acid Journal of the American Chemical Society, vol. 95, 1973, pp. 3021-3023.

Lehn et al Cryptates: stability and selectivity of alkali and alkaline-earth macrobicyclic complexes Journal of the American Chemical Society, 97:23, 1975, pp. 6700-6707.

Läubli et al Barium-selective electrodes based on neutral carriers and their use in the titration of sulfate in combustion products Analytical Chemistry, vol. 57, 1985, pp. 2756-2758.

Qing et al Polarographic adsorptive waves of alkaline-earth metal complexes with thymolphthalexone Talanta, vol. 34, No. 6, 1987, pp. 555-559.

Tsien New calcium indicators and buffers with high selectivity against magnesium and protons: design, synthesis, and properties of prototype structures Biochemistry, vol. 19, 1980, pp. 2396-2404.

Zirino et al Measurement of Cu and Zn in San Diego Bay by automated anodic stripping voltammetry Environmental science and technology, American Chemical Society, vol. 12, No. 1, 1978, pp. 73-79.

Zirino Voltammetry of natural sea water Marine electrochemistry, a practical introduction, edited by Whitfield and Jagner, Wiley 1981, pp. 421-503.

APPARATUS AND METHOD FOR MEASURING CONCENTRATIONS OF SCALE-FORMING IONS

FIELD OF THE INVENTION

This invention relates to the determination of ion concentrations in downhole water from hydrocarbon wells, aquifers etc. This is useful in a wide range of applications, including predicting the formation of scale and fingerprinting waters from different sources.

BACKGROUND

The prediction of the location and type of mineral scale that may form around or within the production or surface facilities of an oil well is an important factor both in the design of the well and the formulation of strategies to cope with the mineral scale.

Current methods for predicting mineral scale formation involve the retrieval of samples from downhole, which are then either analysed at the surface or else sent off to laboratories for analysis. Errors and delays can arise from this ex situ analysis.

Electrochemical methods have previously been developed for the measurement of the concentration of a number of different metal ions, and some have been deployed in shallow boreholes, lakes and ocean waters. However, the application of these methods to oilfield operations has been limited, as the high temperatures (up to 175 Celsius) and pressures (up to 1500 bar) common to most reservoirs, make their use impractical. Furthermore, many electrochemical methods are not able to distinguish between the principal metal ions ($Ca^{2+}$, $Ba^{2+}$ and $Sr^{2+}$) responsible for scale formation. This problem is compounded by the low concentrations of these ions (about 10 s mg/L) in formation water which is often highly saline.

The ability to rapidly and conveniently distinguish scaling ions may also find application, for example, in fingerprinting waters flowing into a hydrocarbon well from different producing zones. This information, which is indicative of connectivity between different zones of a producing well, may allow the optimization of production strategies for recovering the oil in place.

SUMMARY OF THE INVENTION

An object of the invention is to provide improved methods for the measurement of the scaling ions, which are suitable for use in situ i.e. in a continuous connection to a flow of fluid.

Accordingly, a first aspect of the invention provides an apparatus for determining the concentration of scaling ions in downhole water; the apparatus comprising a ligand which binds scaling ions from a flowing fluid, which could be downhole water, said ligand having an electronic configuration which is altered on binding of a scaling ion, and a detector for determining alterations in said electronic configuration, the amount of said alterations being indicative of the concentration of the scaling ion in the sample.

Preferably the ligand is contained within an electrochemical cell and changes in the electroactivity of the ligand are determined, for example amperometrically or voltammetrically. In other embodiments, the binding of a scaling ion may alter the fluorescent properties of the ligand. Changes in the fluorescence of the ligand upon binding of the ligand may be determined using any of a range of conventional techniques.

The apparatus may comprise a single ligand which binds specifically to a single scaling ion, such that changes in the electronic configuration of the ligand are directly related to the concentration of the scaling ion in the sample water.

More preferably, the apparatus may contain two or more different ligands, for example three, four, or five or more. Alterations in the electronic configuration of each ligand may be determined independently, either simultaneously or sequentially.

In some embodiments, each ligand may bind specifically to a different scaling ion. Changes in the electronic configuration of each ligand are directly related to the concentration of the corresponding scaling ion in the sample water.

In other embodiments, each ligand may bind to two or more different scaling ions. Changes in the properties (i.e. the electronic configuration) of each ligand are directly related to the concentration in the sample water of the two or more scaling ions to which that ligand binds. The different electronic response of the ligand to different ions can be translated into a respective concentration measurements, for example by locating the peaks in a voltagram.

Alternatively, each ligand may bind to a different combination of scaling ions such that the concentration of each individual scaling ion in the sample water may be calculated from the measurements determined for two or more different ligands.

An advantage of the apparatus is that it allows in situ analysis to be performed, thereby avoiding the problems associated with transporting samples to the surface for ex situ analysis. The present invention is partly based on the realisation that electrochemical techniques can be adapted for performance downhole, i.e. in relatively demanding and hostile conditions.

Preferably the detector is operably connected to a processor for determining the concentration of scaling ions from the current or potential in the cell.

In some embodiments, the apparatus is adapted for use downhole (i.e. in a hydrocarbon well or aquifer).

The processor may also be adapted for use downhole, or alternatively it may be intended for remote installation e.g. at the surface. For example, the processor may be a suitably programmed computer.

A further aspect of the invention provides for the use of apparatus as described herein for in situ measurement of scaling ion concentration.

In another aspect the invention provides a method of monitoring the concentrations of scaling ions in downhole water comprising;
  contacting a sample of downhole water with a ligand which selectively binds scaling ions, wherein the binding of scaling ions in said sample to the ligand alters the electronic configuration of the ligand;
  measuring changes in the electronic configuration of the ligand; and,
  determining the concentration of said scaling ion from said changes in electronic configuration.

BRIEF DESCRIPTION OF THE FIGURES

Specific embodiments of the invention will now be described with reference to the following drawings, in which.

DETAILED DESCRIPTION OF THE INVENTION

In general terms, the present invention relates to the measurement of concentration of ions in downhole water, in particular ions responsible for scale formation by means of changes in the electronic configuration of a ligand which binds scaling ions. A preferred approach involves the use of an electrochemical cell containing a ligand whose electroactivity changes on binding a scaling ion. Changes in ligand electroactivity upon ion binding alter the electrochemical properties of the cell and may be measured using a detector. Other approaches may comprise the use of a ligand whose fluorescent properties change on binding of a scaling ion.

Downhole water may be comprised within a production fluid from a hydrocarbon well or reservoir, which may comprise hydrocarbons, drilling mud etc. The downhole water may, for example, be connate water.

Scaling ions are ions which are responsible for the formation of scale. The principal scaling ions in downhole water are $Ca^{2+}$, $Ba^{2+}$ and $Sr^{2+}$. A suitable ligand may bind selectively to one or more of these scaling ions e.g. a ligand may bind to $Ca^{2+}$, $Ba^{2+}$ and $Sr^{2+}$. Preferably, a ligand shows substantially no binding to other ions.

In some embodiments, the ligand may have a different binding affinity for each of the three principal scaling ions ($Ca^{2+}$, $Ba^{2+}$ and $Sr^{2+}$), allowing the levels of each individual ion in the downhole water to be determined. Discrimination between different ligands may be achieved, for example, by determining the characteristic redox properties of each ligand at different potentials.

The ligand may be present in the cell in an aqueous solution at a concentration of 0.1 to 10 mM, preferably 1 to 10 mM, or may be dispersed within a porous polymer membrane.

Ligands suitable for use in accordance with the invention are stable and able to bind scaling ions under downhole conditions, for example at high temperature (e.g. up to 175° C.) and pressure (e.g. up to 1500 bar).

One class of suitable ligands have the formula (I):

where R1 is a $C_{1-5}$ alkyl (including, e.g. unsubstituted $C_{1-5}$ alkyl and substituted $C_{1-5}$ alkyl) or $C_{1-8}$ aryl (including, e.g. unsubstituted $C_{1-8}$ aryl and substituted $C_{1-8}$ aryl); and, R2 to R9 may independently be H, halogen (F, Cl, Br, I); $C_{1-5}$ alkyl group; O—$C_{1-5}$ alkyl group; COOH; NH2; —CONH2; CO—$C_{1-5}$ alkyl group; or a fluorophore group such as carboxy-X-rhodamine (ROX), tetramethylrhodamine (TAMRA) and fluorescein (FAM).

"$C_{1-5}$ alkyl" pertains to a monovalent moiety obtained by removing a hydrogen atom from a $C_{1-5}$ hydrocarbon compound having from 1 to 5 carbon atoms, which may be aliphatic or alicyclic, or a combination thereof, and which may be saturated, partially unsaturated, or fully unsaturated.

Examples of suitable ligands according to formula I are shown in FIG. 2.

In some embodiments, the aromatic rings of suitable ligands may comprise substitutions in the ortho, meta or para positions (i.e. at one or more of positions R2 to R9), in order to shift the redox features of a ligand to allow scanning for the different ions in well-separated spectral windows, in order to prevent interference.

For the purpose of this invention the above class of ligands are referred to as O,O'-Bis(2-aminophenyl) ethyleneglycol-N,N,N',N'-tetraacetic acid or BAPTA derivatives.

Other suitable ligands may include cryptands (Lehn & Sauvage (1975) J. Am. Chem. Soc. 97 23 6700), for example a ligand shown in FIG. 3, and thymolphthalein and their derivatives (Qing and Yuying (1987) Talanta 34 6 555), for example ligands shown in FIG. 4. Other suitable ligands may include neutral ionophores (Simon et al Anal. Chem. 1985, 57, 2756), specific crown ethers (D. J. Cram et al J. Am. Chem. Soc., 1973, 95, 3021) or antibiotics such as valinomycin.

Figure 5:
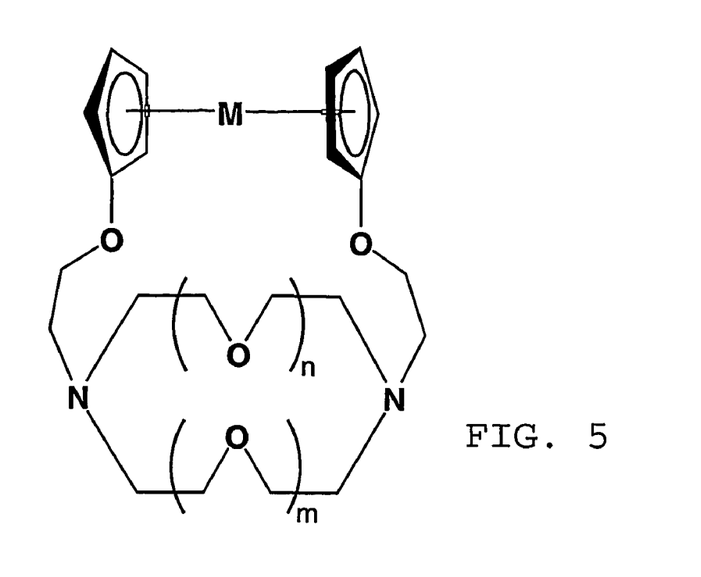

A further ligand of the cryptand family is shown in FIG. 5. The cryptand is derivatized by a redox-active group or moiety M. The entity M can be selected for example from a group consisting of Fe, Ru, Co, V, Cr, Mo, and W and n and m can range from 1 to 3.

Figure 3:
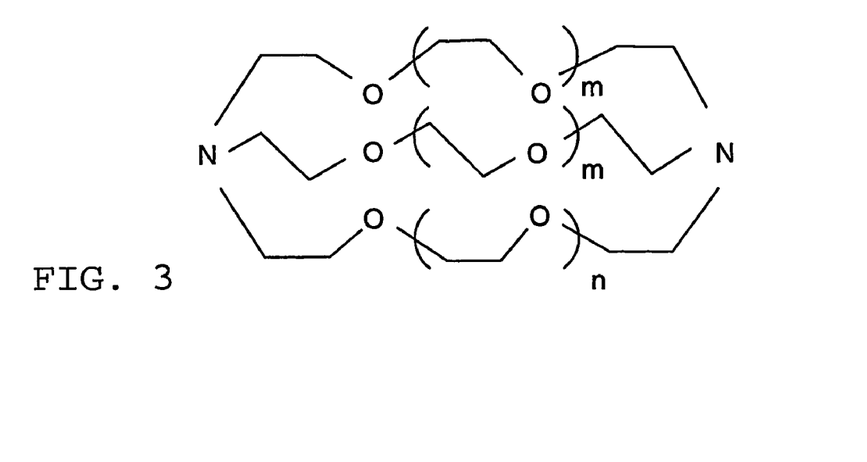

For the purpose of this invention, ligands of the type of FIGS. 3 and 5 are referred to as cryptand derivatives.

The Apparatus May Further Comprise a Porous Membrane or porous electrode block which allows ions within the downhole water to pass into the cell to contact the ligand. A suitable porous membrane may be made of zeolite or a ceramic material. A block may be made of epoxy material as base material.

The membrane may be contacted with discrete samples or batches of downhole water or the membrane may be contacted with a continuous flow of downhole water. The apparatus may comprise one or more liquid guidance channels to direct downhole water to the membrane and to remove downhole water after contact with the membrane.

The detector may comprise one or more electrodes which contact the ligand. Various arrangements of electrodes may be used as is conventional in electrochemistry.

Conveniently a three-electrode arrangement consisting of a working electrode, a reference electrode and a counter electrode may be used. Preferably, the working electrode is composed of a material resistant to fouling, such as boron-doped diamond or glassy carbon, the counter electrode is platinum and the reference electrode is Ag/AgCl. Other suitable electrode materials, such as AgI, are known to those skilled in the art.

The electrodes may be used to detect changes in the electroactivity of the one or more ligands. For example, electroactivity changes caused by the presence of scaling ions may alter the current flow or voltage between electrodes. Current or voltage may be detected or measured by the detector. For example, the potential of the electrodes may be varied and the current measured or vice versa. The current or potential difference associated with the electroactivity of each of the one or more ligands may be measured by the detector and correlated with the concentration of scaling ions in the downhole water sample. In the presence of the target ions, the peak current(s) should increase, proportional to the concentration of the target species. A power source may be connected to the electrodes to drive the current between the electrodes. The power source may be an integral part of the apparatus, and, for example, may be comprised within the detector. In other embodiments, the power source may be separate from the apparatus and connectable thereto. The apparatus may comprise appropriate circuitry for connection to the power source.

The ligand may be contained within the apparatus in any of a number of ways. In some embodiments, the ligand may be dispersed in an aqueous solution within a chamber of the apparatus. In other embodiments, the ligand may be dispersed within a porous polymer membrane. Binding of the scaling ions by the ligand occurs within the pores of the membrane and resultant changes in current or potential are detected by circuitry connected directly to the membrane via the working, counter and reference electrodes. The use of a porous membrane is convenient in allowing the miniaturisation of the voltammetric or amperometric sensor, thus leading to faster response times, lower consumption of reagents and lower unit costs.

In other embodiments, the ligands may be attached to conducting solid particles, such as carbon or a metal (e.g., gold), which are incorporated into the surface of one or more of the electrodes, preferably, the working electrode. The accumulation of particles with attached ligand forms a conducting porous electrode with ligand attached to the walls of the pores. Suitable techniques for fixing the particles to the electrode surface include epoxy resin adhesion or abrasive immobilisation. A porous electrode for hydrogen sulfide determination, for example, is described in co-pending published United Kingdom application GB-A-2391314.

For example, the ligand (I) above may be designed such that group R8 is an amine (—$NH_2$), which can be reacted with nitrous acid to form the diazonium ion —$N_+$≡$N$ and subsequently coupled to carbon particles by reduction of the diazonium group by hypophosphorous acid. The ligand is thus chemically bonded to the carbon particles and these can be incorporated into the working electrode 4 as described above. In other embodiments, the ligand (I) above may be coupled to gold particles with one of the groups R2 to R9 being either an amine (—$NH_2$) or a thiol (—SH).

As described above, the detector may be operably connected to a processor that determines the concentration of scaling ions in the sample from the current or potential difference measured by the detector. The processor may be separate from or part of the detector. The processor may also be adapted for use under downhole conditions (i.e. high temperature, high pressure and high salinity). Alternatively, it may be intended for remote installation e.g. at the surface. For example, the processor may be a suitably programmed computer.

The measurement of scaling ion concentrations as described herein may be useful in downhole sampling, production logging to characterise flow into the well, and thereby aid remediation or production strategies, and in permanent monitoring applications, where the build up of scale or water breakthrough/flooding of the reservoir might be gauged.

Figure 1A:
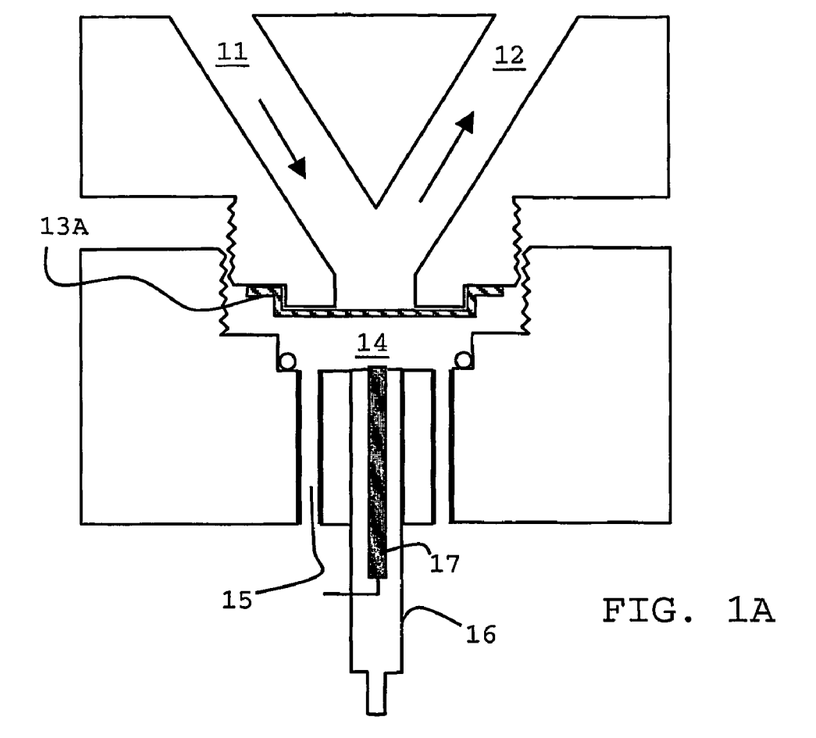
FIGS. 1A and 1B show examples of an apparatus according to the invention.

FIG. 1A shows a cross-sectional diagram of an apparatus according to one embodiment of the invention. The apparatus is shown separated into an upper and a lower part as in a stage of being assembled. Inlets 11 and outlets 12 for sampling downhole water are indicated by arrows pointing in the direction of the flow. The sample water contacts a membrane 13A which allows the passage of ions into the cell 14. The ligand solution in the cell 14 is contacted by a Ag/AgCl reference electrode 15, a platinum ring counter electrode 16 and a glassy carbon working electrode 17. The electrodes 15, 16 and 17 detect changes in the electroactivity of ligand in the cell 14 which are related to scaling ion concentration.

Figure 1B:
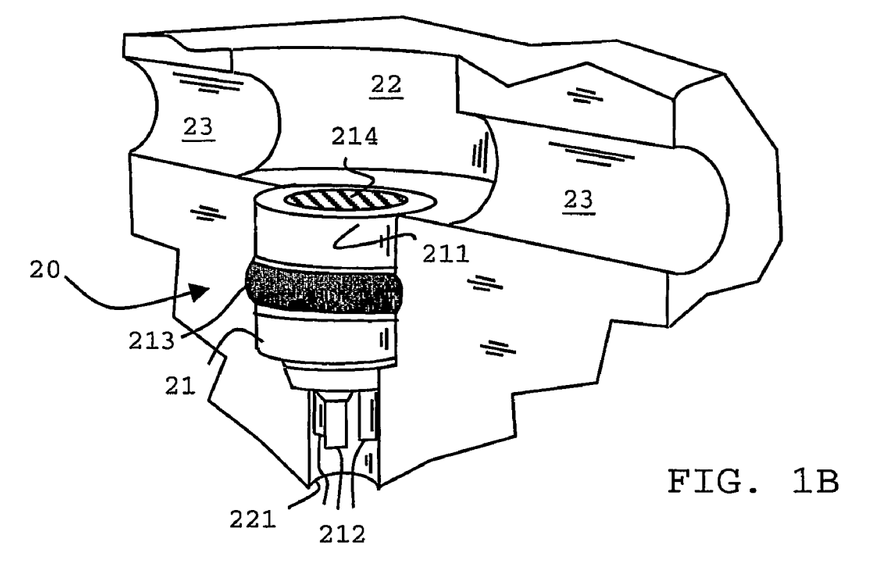

In the variant of FIG. 1B, a scale sensor 20 is shown coupled to a flowline 23. The body 21 of the sensor is fixed into the end section of an opening 22. The body carries a microporous epoxy matrix 211 embedding the catalysts 214 and contacts 212 that provide connection points to voltage supply and measurement through a small channel 221 at the bottom of the opening 22. A sealing ring 213 protects the contact points and electronics from the wellbore fluid that passes under operation conditions through the sample channel 23.

In an example according to an embodiment of the invention, the four ligands (2A-2D) shown in FIG. 2 may be present in solution in cell 14 or embedded in block 211.

These ligands have different binding properties; ligand 2A binds $Ca^{2+}$, $Sr^{2+}$ and $Ba^{2+}$; ligand 2B binds $Ca^{2+}$ and $Sr^{2+}$, ligand 2C binds $Sr^{2+}$ and $Ba^{2+}$ and ligand 2D binds $Ba^{2+}$.

Figure 2A:
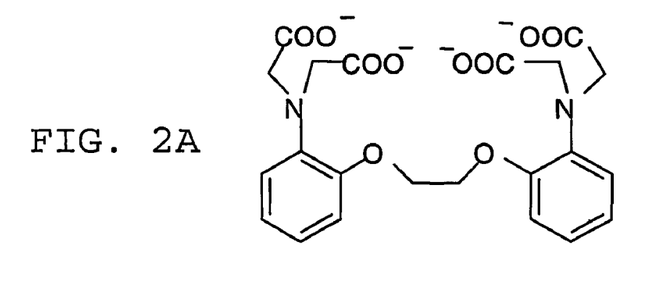
FIGS. 2 to 5 show examples of ligands suitable for use in accordance with the invention.
Figure 2B:
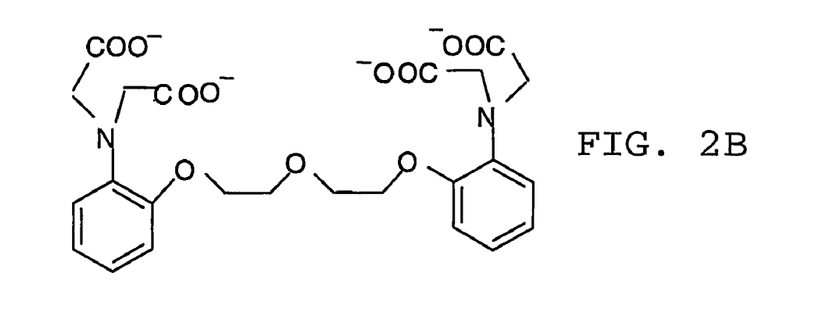
Figure 2C:
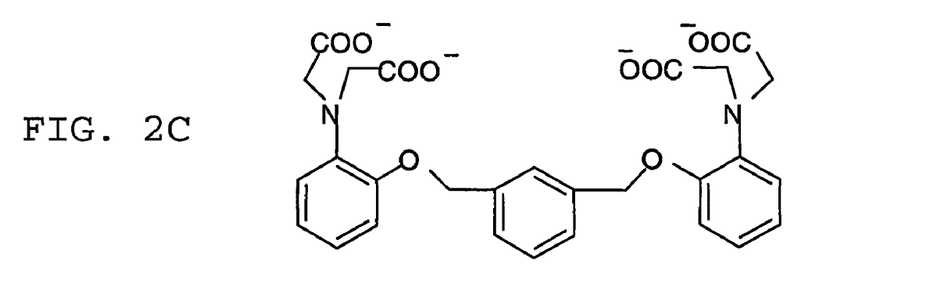
Figure 2D:
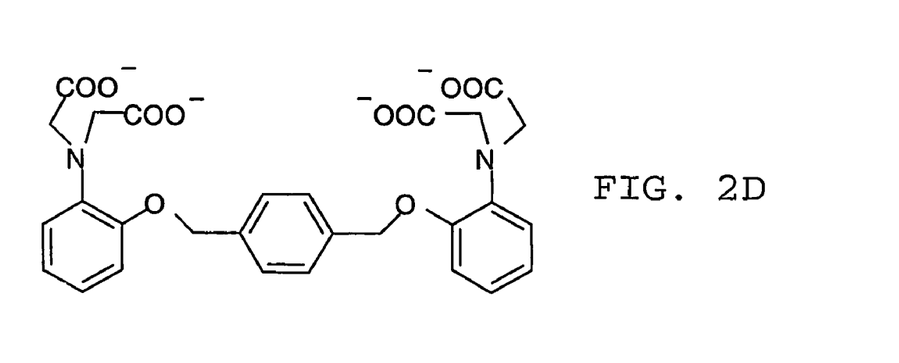

The level of $Sr^{2+}$ in the sample water may be determined, for example, by measuring the alterations of the electroactivities of ligands 2C and 2D in the cell and then subtracting the value obtained for ligand 2D from value obtained for ligand 2C, to provide a value which represents the concentration of $Sr^{2+}$. (i.e. 2C−2D=[$Sr^{2+}$]). As above the figure label is taken as a representative of the respective ligand and/or the concentration measurement associated with it.

The level of $Ca^{2+}$ in the sample water may be determined by measuring the alterations of the electroactivities of ligands 2B, 2C and 2D in the cell. The values for ligands 2B and 2D are added together and the value obtained for ligand 2C is subtracted from this combined figure, to provide a value which represents the concentration of $Ca^{2+}$. (i.e. 2B+2D−2C=[$Ca^{++}$]).

The level of $Ba^{2+}$ in the sample water is determined by measuring the alterations of the electroactivities of ligands 2A and 2B in the cell and then subtracting the value obtained for ligand 2B from the value obtained for ligand 2A, to provide a value which represents the concentration of $Ba^{2+}$. (i.e. 2A−2B=[$Ba^{2+}$] or ligand 2D).

Figure 4A:
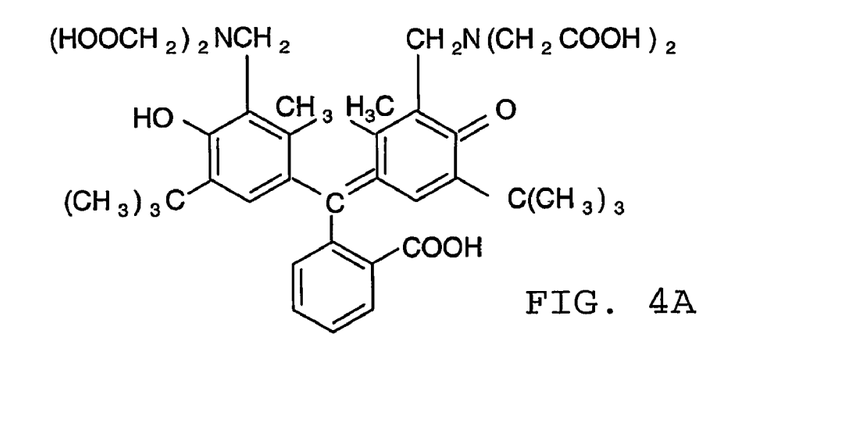
Figure 4B:
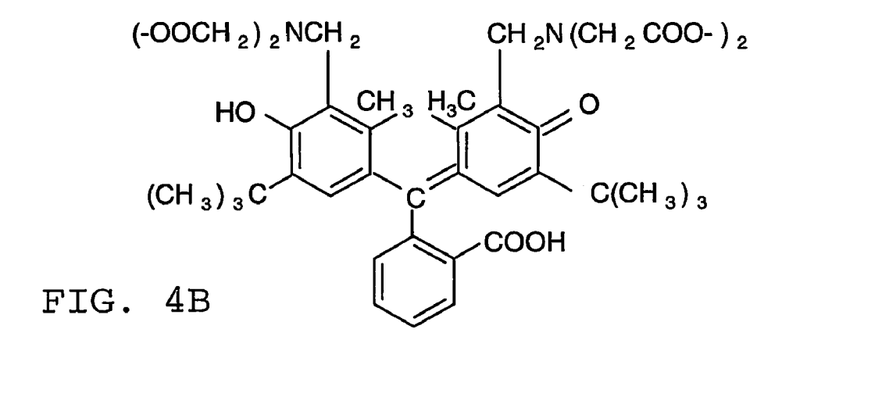

The chemical structure of further examples of ligands are shown in FIGS. 3 and 4. The indices n and m of the ligand in FIG. 3 can be 1 or 2. FIG. 5 shows the example of a cryptand modified with a redox active moiety. The entity M can be selected from a group consisting of Fe, Ru, Co, V, Cr, Mo, and W and n and m can range from 1 to 3.

Figure 6:
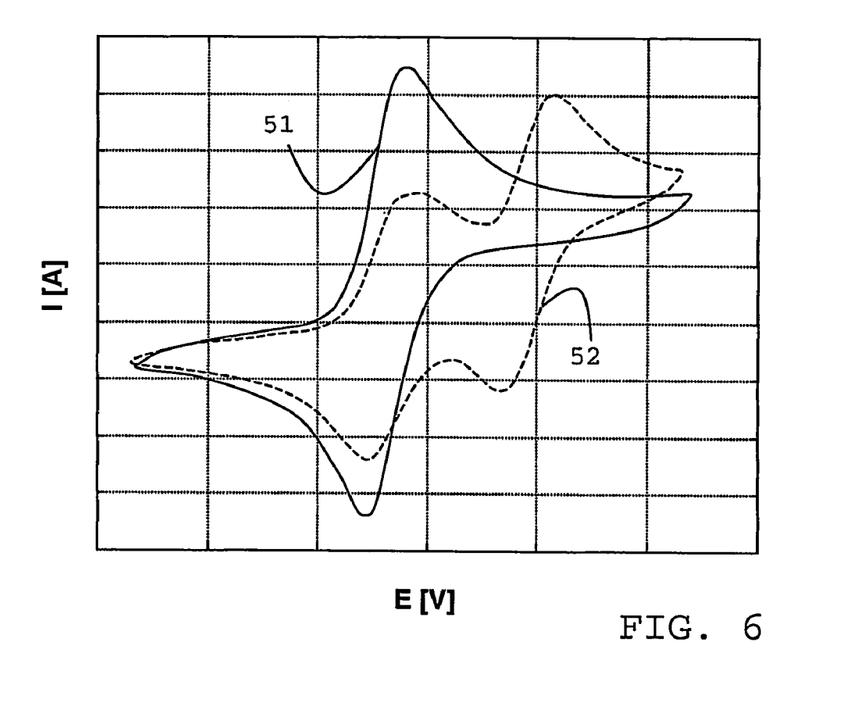
FIG. 6 shows a voltagram measured using a ligand of FIG. 5 in an ion-free fluid and a fluid with Ba-ions.

In FIG. 6 there is shown the response of the ligand of FIG. 5 with M=Fe and n=m=2 to the presence of $Ba^{2+}$. The solid line 51 is the typical electrochemical response of the pure ligand, whereas the dashed line 52 is the same response in the presence of Ba cations. The ligand of FIG. 5 is sensitive to more than one species of scale-forming ions and the presence of different ions can be readily detected from determining the peak locations in the voltagramm. This ligand thus alleviates the need to use multiple ligands. Square wave voltametry may be used instead of the shown full cycle voltametry.

Figure 7:
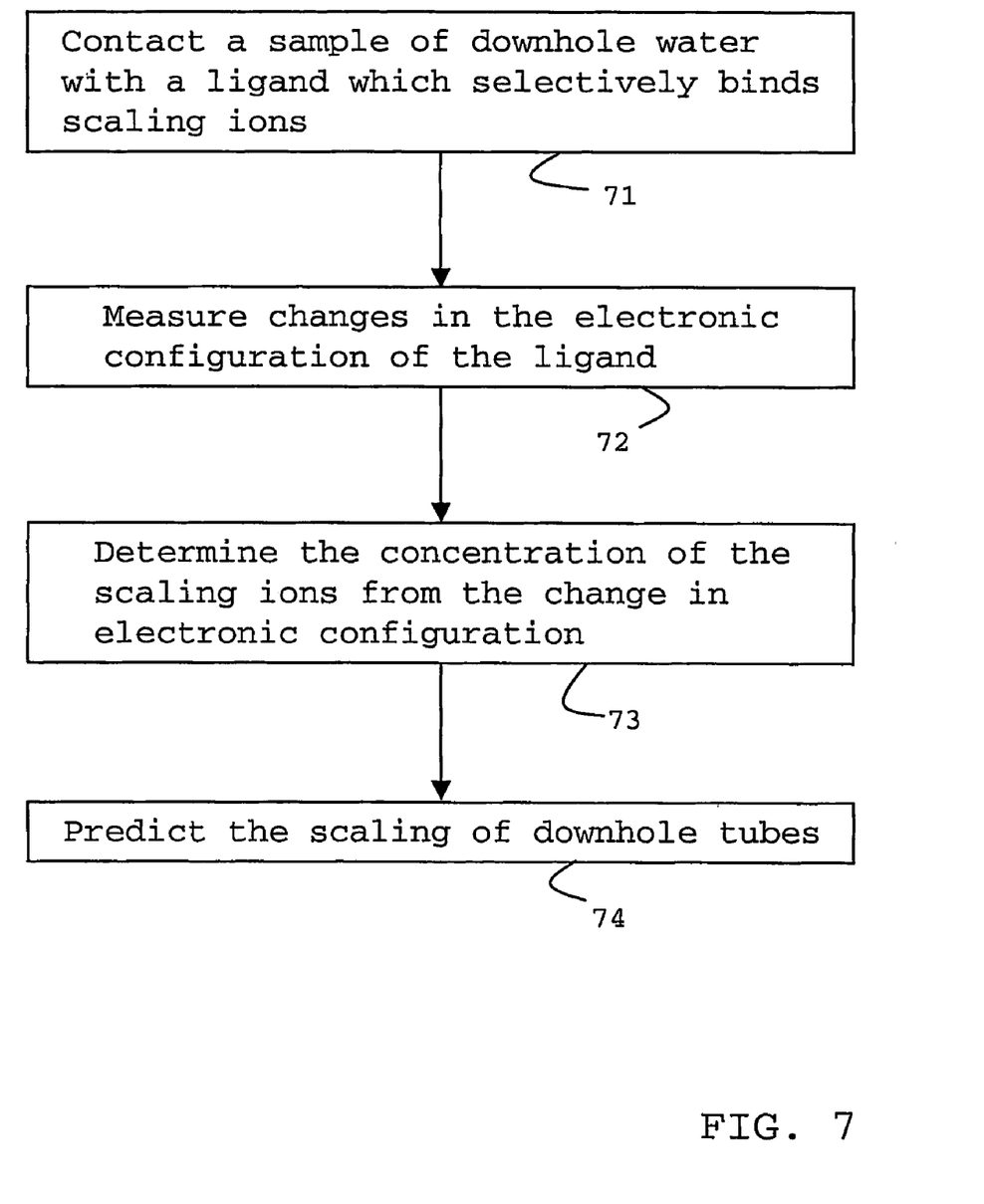
FIG. 7 shows a flow diagram of a method in accordance with an example of the present invention.

The flowchart of FIG. 7 summarizes steps of a method exemplary of the present invention, including the step 71 of contacting a sample of for example downhole water with a ligand which selectively binds scaling ions, the step 72 of measuring changes in the electronic configuration of the ligand, and the step 73 of determining the concentration of the scaling ions from the change in electronic configuration. The results of the measurement may be fed into a model 74 that predicts the built-up of scaling in tubulars and other flow exposed equipment, for example production tubing or downhole pumps.

Figure 8:
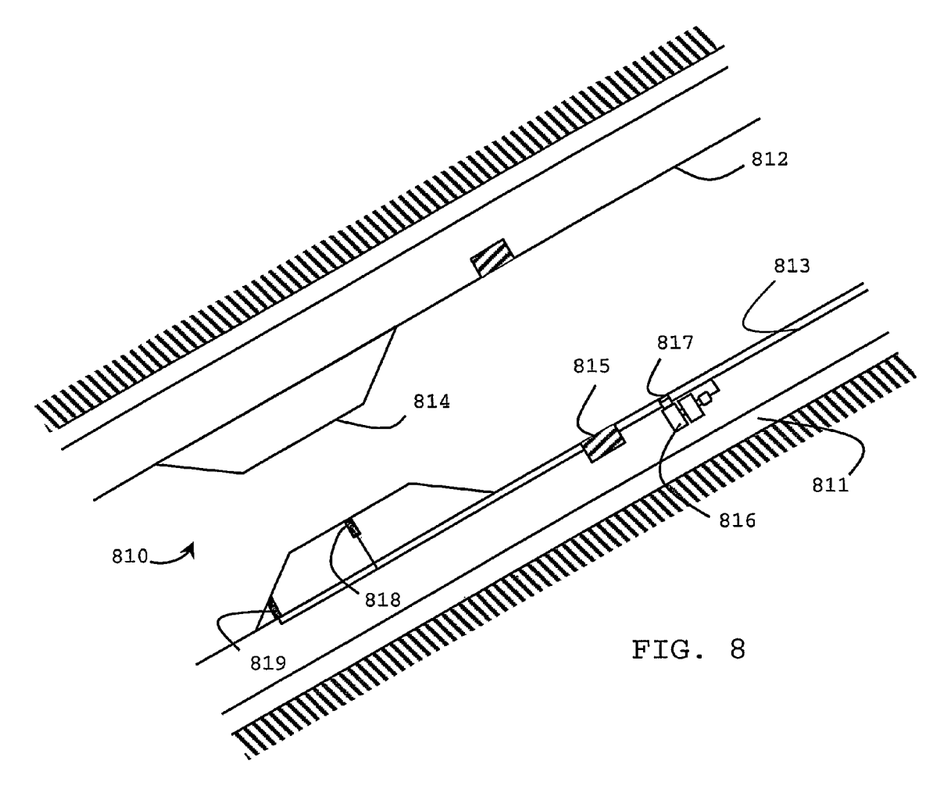
FIG. 8 shows an example of a scale sensor in a downhole application.

An application of the sensor is illustrated in FIG. 8. It shows a Venturi-type flowmeter 810, as well known in the industry and described for example in the U.S. Pat. No. 5,736,650. Mounted on production tubing or casing 812, the flowmeter is installed at a location within the well 811 with a wired connection 813 to the surface following known procedures as disclosed for example in the U.S. Pat. No. 5,829,520.

The flowmeter consists essentially of a constriction or throat 814 and two pressure taps 818, 819 located conventionally at the entrance and the position of maximum constriction, respectively. Usually the Venturi flowmeter is combined with a densiometer 815 located further up- or downstream.

The novel scale sensor 816 is preferably located downstream from the Venturi to take advantage of the mixing effect the Venturi has on the flow. A recess 817 protected by a metal mesh provides an inlet to the unit.

During production wellbore fluid enters the recess 817 and is subsequently analyzed using sensor unit 816. The results are transmitted from the data acquisition unit to the surface via wires 813.

While the invention has been described in conjunction with the exemplary embodiments described above, many equivalent modifications and variations will be apparent to those skilled in the art when given this disclosure. Accordingly, the exemplary embodiments of the invention set forth above are considered to be illustrative and not limiting. Various changes to the described embodiments may be made without departing from the spirit and scope of the invention.

The invention claimed is:

1. An apparatus for determining the concentration of scale-forming ions; the apparatus comprising:
a ligand which binds scaling ions in a sample of fluid, said ligand having an electronic configuration which is altered on binding of a scaling ion, wherein the ligand is a BAPTA derivative and said ligand is configured to be placed in the vicinity of a flow of said fluid; and
a detector for determining alterations in said electronic configuration, the amount of said alterations being indicative of the concentration of the scaling ion in the sample.

2. An apparatus according to claim 1 wherein the scaling ion is selected from the group consisting of Ca2+, Ba2+ and Sr2+ ions.

3. An apparatus according to claim 1 wherein the ligand is immobilised on conducting particles attached to one or more of said electrodes.

4. An apparatus according to claim 3 such that wherein said conducting particles are carbon or metal particles.

5. An apparatus according to claim 4 wherein the metal particles are gold particles.

6. An apparatus according to claims 3 wherein said particles with immobilised ligands thereon form a conducting porous electrode.

7. An apparatus according to claim 1 comprising a processor for calculating the concentration of the scaling ion in the sample from alterations in the electronic configuration of the ligand.

8. An apparatus according to claim 7 wherein the ligand binds two or more different scaling ions and generates a different electronic configuration in response thereto.

9. An apparatus according to claim 7 comprising two or more different ligands, said detector being adapted to determine alterations in the electronic configuration of each of the different ligands independently.

10. An apparatus according to claim 9 wherein each of the said two or more ligands binds to a different combination of scaling ions.

11. An apparatus according to claim 1 further comprising a porous membrane which allows ions from the fluid to contact the ligand.

12. An apparatus according to claim 11 wherein the membrane is ceramic or zeolite.

13. An apparatus according to claim 1 wherein the ligand is embedded in a block of porous material, said block being exposed to the fluid flow.

14. An apparatus according to claim 1 wherein the fluid is a wellbore effluent.

15. An apparatus according to claim 1 wherein the fluid stems from a production flow from a wellbore.

16. An apparatus according to claim 1 being adapted to be placed in a subterranean location.

17. A method of monitoring the concentrations of scaling ions comprising:
contacting a fluid flow with a ligand which selectively binds scaling ions, wherein the binding of scaling ions in said sample to the ligand alters the electronic configuration of the ligand, wherein the ligand is a BAPTA derivative;
measuring changes in the electroactivity of the ligand with one or more electrodes; and determining the concentration of said scaling ion from said changes in said electroactivity of said ligand.

18. A method according to claim 17 wherein the scaling ions are selected from the group consisting of Ca2+, Ba2+ and Sr2+ ions.

19. A method according to claim 17 comprising contacting the sample with two or more different ligands and determining alterations in the electronic configuration of each of the two or more ligands.

20. A method according to claim 19 wherein each of the said two or more ligands binds to a different combination of scaling ions.

21. A method according to claim 17 including the step of monitoring the production of a wellbore.

22. A method according to claim 17 including the step of predicting the scaling of hydrocarbon production tubulars or equipment.

23. A method according to claim 17 including the step of monitoring the scaling of hydrocarbon production tubulars or equipment in a downhole location.

24. A method according to claim 17 wherein the ligand binds two or more different scaling ions and generates a different electronic configuration in response thereto.

* * * * *